(12) United States Patent
Toyota et al.

(10) Patent No.: US 11,477,999 B2
(45) Date of Patent: Oct. 25, 2022

(54) METHOD FOR PRODUCING WHEY PROTEIN HYDROLYSATE

(71) Applicant: MEIJI CO., LTD., Tokyo (JP)

(72) Inventors: Kenji Toyota, Kanagawa (JP); Nobutaka Yahiro, Kanagawa (JP)

(73) Assignee: MEIJI CO., LTD., Tokyo (JP)

(*) Notice: Subject to any disclaimer, the term of this patent is extended or adjusted under 35 U.S.C. 154(b) by 31 days.

(21) Appl. No.: 16/344,523

(22) PCT Filed: Oct. 30, 2017

(86) PCT No.: PCT/JP2017/039059
§ 371 (c)(1),
(2) Date: Apr. 24, 2019

(87) PCT Pub. No.: WO2018/079762
PCT Pub. Date: May 3, 2018

(65) Prior Publication Data
US 2019/0239538 A1 Aug. 8, 2019

(30) Foreign Application Priority Data
Oct. 31, 2016 (JP) .............................. JP2016-213801

(51) Int. Cl.
| | |
|---|---|
| *A23J 3/34* | (2006.01) |
| *A23J 3/08* | (2006.01) |
| *C12P 21/06* | (2006.01) |
| *A23L 33/19* | (2016.01) |
| *C12N 9/50* | (2006.01) |

(52) U.S. Cl.
CPC ............... *A23J 3/347* (2013.01); *A23J 3/08* (2013.01); *A23J 3/341* (2013.01); *A23L 33/19* (2016.08); *C12P 21/06* (2013.01); *C12N 9/50* (2013.01)

(58) Field of Classification Search
CPC .... A23L 33/19; A23J 3/08; A23J 3/341; A23J 3/343; C12P 21/06; C12N 9/50
See application file for complete search history.

(56) References Cited

U.S. PATENT DOCUMENTS

| | | | | |
|---|---|---|---|---|
| 4,847,096 | A | * 7/1989 | Mellqvist | A23J 3/343 426/41 |
| 5,744,179 | A | 4/1998 | Shimamura et al. | |
| 2014/0004152 | A1 | * 1/2014 | Affolter | A61K 38/018 424/275.1 |

FOREIGN PATENT DOCUMENTS

| | | |
|---|---|---|
| JP | 63-160555 | 7/1988 |
| JP | 3071877 | 1/1993 |
| JP | 6-165655 | 6/1994 |
| JP | 8-98656 | 4/1996 |
| JP | 8-173093 | 7/1996 |
| JP | 11-18724 | 1/1999 |
| JP | 11-509727 | 8/1999 |
| JP | 2006-67874 | 3/2006 |
| JP | 2006-75064 | 3/2006 |
| JP | 2007-215540 | 8/2007 |
| JP | 2009-261299 | 11/2009 |
| JP | 2009-539883 | 11/2009 |
| JP | 2012-522498 | 9/2012 |
| WO | 94/12053 | 6/1994 |
| WO | 97/01966 | 1/1997 |
| WO | WO-9701966 A1 * | 1/1997 .............. A23J 3/343 |
| WO | 2007/143794 | 12/2007 |
| WO | 2010/112546 | 10/2010 |

OTHER PUBLICATIONS

Novozymes brochure, "Proteases for Biocatalysis" Jun. 2016, all references cited are prior to 2010. (Year: 2016).*
De Castro, R.J.S. et al. 2014. Advantages of an acid protease from Aspergillus oryzae over commercial preparations for production of whey protein hydrolysates with antioxidant activities. Biocatalysis and Agricultural Biotechnology 3: 58-65. specif. pp. 58, 59, 64.*
Liaw, I.W. et al. 2010. The impact of antioxidant addition on flavor of Cheddar and mozzarella whey and Cheddar whey protein concentrate. Journal of Food Science 75(6): C559-C569. specif. p. C559.*
Gallardo-Escamilla, F.J. et al. 2005. Sensory characteristics and related volatile flavor compound profiles of different types of whey. Journal of Dairy Science 88: 2689-2699. specif. pp. 2689, 2692.*
Melenteva, A. et al. Jan. 29, 2016. Building global models for fat and total protein content in raw milk based on historical spectroscopic data in the visible and short-wave near infrared range. Food Chemistry 203: 190-198; specif. pp. 191, 192.*
International Search Report, dated Jan. 16, 2018 in corresponding International Patent Application No. PCT/JP2017/039059, with English language translation.

* cited by examiner

*Primary Examiner* — Olivia M. Wise
*Assistant Examiner* — Sharon M. Papciak
(74) *Attorney, Agent, or Firm* — Wenderoth, Lind & Ponack, L.L.P.

(57) ABSTRACT

The present invention relates to a method for producing a whey protein hydrolysate, the method comprising subjecting a whey protein-containing starting material having (a) a lipid content of less than 1 mass % and/or (b) a lactose content of less than 1 mass % to hydrolysis treatment. According to the present invention, a whey protein hydrolysate having excellent flavor with reduced odor is produced by reducing the problems involving rough taste, bitterness, or an unpleasant odor caused by hydrolysis of whey proteins. It is also possible to produce a whey protein hydrolysate that is not easily discolored, and that is prevented from being degraded in quality during the production process and storage thereof.

26 Claims, 3 Drawing Sheets

(A)

(B)

(A)

(B)

(A)

(B)

METHOD FOR PRODUCING WHEY PROTEIN HYDROLYSATE

TECHNICAL FIELD

The present invention relates to a method for producing a whey protein hydrolysate having excellent flavor. The present invention also relates to a method for producing a whey protein hydrolysate in which time-dependent discoloration caused by storage etc. is suppressed.

BACKGROUND ART

For the purpose of improving absorbency or reducing allergens, whey protein is often degraded by a proteolytic enzyme (a protease) to whey protein hydrolysates.

However, hydrolysis of whey protein causes the occurrence of characteristic rough taste, unpleasant odor, or bitterness that is attributable to peptides or free amino acids, undesirably deteriorating the flavor. Further, whey protein hydrolysates are easily discolored, in particular, when heated in the state of an aqueous solution, and are known to cause deterioration in quality during the production process or storage thereof.

Therefore, various methods have been proposed for improving the flavor of whey protein hydrolysates. Examples of known methods include a method for obtaining a whey protein peptide composition having excellent flavor, the method comprising mixing whey protein and lactose, or mixing whey protein, lactose, and/or desalted whey protein, followed by enzymatic degradation (Patent Literature (PTL) 1); a method for obtaining a food composition with reduced bitterness and astringency by using a shiitake mushroom extract and nucleic acids of sodium inosinate, sodium guanylate, etc., together with whey peptide, and a method for enhancing the masking effect by further blending acetic acid and/or a tea extract (both PTL 2); a method for reducing bitterness by adding an acidic phospholipid to amino acids or peptides, which produce bitterness (PTL 3); a method for reducing bitterness or odor of peptides by adding cyclodextrin to food products containing peptides (including peptides from milk proteins) (PTL 4); a method for reducing bitterness or odor of peptides caused by photo- and/or thermal degradation, the method comprising adding one or more flavonoids and/or gallic acid derivatives to beverages containing peptides (including peptides from milk proteins) (PTL 5); a method for obtaining a low-allergenic enzymolysis peptide composition having oral tolerogenic ability and excellent flavor with low antigenicity, the method comprising treating protein from cow milk with a proteolytic enzyme to obtain a peptide with a molecular weight of 10,000 or less (PTL 6); and the like. Among these, however, the techniques disclosed in PTL 1, PTL 2, PTL 3, PTL 4, and PTL 5 are all for masking bitterness and odor by adding other components, and the technique disclosed in PTL 6 is a method for controlling the hydrolysis degree. These techniques suffer from problems such that the flavor is undesirably standardized due to the added substances; they are costly; and the manufacturing processes thereof are complicated.

Examples of known methods for hydrolyzing proteins using an enzyme include a method for hydrolyzing a protein using an enzyme in the presence of dextrin (PTL 7); a method for preparing a hydrolysate with TNF-α expression inhibitory effect, the method comprising hydrolyzing a milk serum protein using an enzyme (PTL 8); and a method for hydrolyzing a milk-derived protein using a specific enzyme (PTL 9). However, none of these documents discloses or suggests a method for improving and enhancing the flavor of whey protein hydrolysates.

CITATION LIST

Patent Literature

PTL 1: JPH08-098656A
PTL 2: JP2009-261299A
PTL 3: JPH08-173093A
PTL 4: JP2006-075064A
PTL 5: JP2006-067874A
PTL 6: JP3071877B
PTL 7: JP2007-215540A
PTL 8: JP2009-539883A
PTL 9: JP2012-522498A

SUMMARY OF INVENTION

Technical Problem

An object of the present invention is to solve the above-described conventional problems regarding hydrolysis of whey protein. More specifically, an object of the present invention is to provide a method for producing a whey protein hydrolysate having excellent flavor, with reduced odor, by reducing problems involving rough taste, bitterness, or unpleasant odor that occur when whey protein is hydrolyzed. Another object of the present inventing is to provide a method for producing a whey protein hydrolysate that is not easily discolored, and that is prevented from being degraded in quality during the production process and storage thereof.

Solution to Problem

The present inventors conducted extensive research to solve the above problems, i.e., to improve the flavor of whey protein hydrolysates; and found that a whey protein hydrolysate that has excellent flavor with reduced odor and that can thus achieve the above objects can be obtained by using a whey protein-containing starting material having a small lipid content, preferably having a lipid content of less than 1 mass %, as a starting material (reaction substrate) for producing whey protein hydrolysates. The present inventors further found that a whey protein hydrolysate in which discoloration by heating is significantly suppressed can be obtained by using a whey protein-containing starting material having a small lactose content, preferably having a lactose content of less than 1 mass %, as a starting material (reaction substrate).

The present invention has been completed based on these findings, and encompasses the following embodiments.
(I) Method for Producing Whey Protein Hydrolysate
(I-1) A method for producing a whey protein hydrolysate, the method comprising hydrolyzing a whey protein-containing starting material having (a) a lipid content of less than 1 mass % and/or (b) a lactose content of less than 1 mass % to prepare a whey protein hydrolysate.
(I-2) The production method according to (I-1), wherein the lipid content and the lactose content of the whey protein-containing starting material are both less than 1 mass %.
(I-3) The production method according to (I-1) or (I-2), wherein the hydrolysis treatment is an enzymatic treatment.

(I-4) The production method according to (I-3), wherein the enzymatic treatment is a treatment that uses a proteolytic enzyme (a protease), preferably Protease M and/or Protease P.

(I-5) The production method according to any one of (I-1) to (I-4), which is a method for obtaining a whey protein hydrolysate with less odor than whey protein hydrolysates obtained by hydrolyzing a whey protein-containing starting material having a lipid content of more than 4 mass %.

(I-6) The production method according to any one of (I-1) to (I-5), which is a method for obtaining a whey protein hydrolysate having more excellent flavor than whey protein hydrolysates obtained by hydrolyzing a whey protein-containing starting material having a lipid content of more than 4 mass %. In this case, a whey protein-containing starting material having at least (a) a lipid content of less than 1 mass % is used as the whey protein-containing starting material.

(I-7) The production method according to any one of (I-1) to (I-6), which is a method for obtaining a whey protein hydrolysate in which time-dependent discoloration is suppressed more than in whey protein hydrolysates obtained by hydrolyzing a whey protein-containing starting material having a lactose content of more than 4 mass %. In this case, a whey protein-containing starting material having at least (b) a lactose content of less than 1 mass % is used as the whey protein-containing starting material.

(II) Method for Reducing Odor, Enhancing Flavor, or Suppressing Discoloration of Whey Protein Hydrolysate (II-1) A method for reducing odor and/or enhancing flavor of a whey protein hydrolysate, the method comprising subjecting a whey protein-containing starting material having a lipid content of less than 1 mass % to hydrolysis treatment to prepare a whey protein hydrolysate.

(II-2) The method for reducing odor and/or enhancing flavor according to (II-1), wherein the whey protein-containing starting material has a lactose content of less than 1 mass %.

(II-3) A method for suppressing discoloration of a whey protein hydrolysate, the method comprising subjecting a whey protein-containing starting material having a lactose content of less than 1 mass % to hydrolysis treatment to prepare a whey protein hydrolysate.

(II-4) The discoloration suppressing method according to (II-3), wherein the lipid content of the whey protein-containing starting material is less than 1 mass %.

(II-5) The method according to any one of (II-1) to (II-4), wherein the hydrolysis treatment is an enzymatic treatment.

(II-6) The method according to (11-5), wherein the enzymatic treatment is a treatment that uses a proteolytic enzyme (a protease), preferably Protease M and/or Protease P.

Advantageous Effects of Invention

Protein hydrolysis using a whey protein-containing starting material having a lipid content of less than 1 mass % can yield a whey protein hydrolysate with reduced odor. This whey protein hydrolysate has excellent flavor with reduced bitterness and rough taste, compared to whey protein hydrolysates prepared by using a whey protein-containing starting material having a lipid content of more than 4 mass %. Moreover, protein hydrolysis using a whey protein-containing starting material having a lactose content of less than 1 mass %, preferably a whey protein-containing starting material having a lipid content of less than 1 mass % and a lactose content of less than 1 mass %, can yield a whey protein hydrolysate in which time-dependent discoloration is suppressed, in addition to having the above characteristics (reduced odor and excellent flavor), compared to whey protein hydrolysates prepared by using a whey protein-containing starting material having a lactose content of more than 4 mass %. In the thus-prepared whey protein hydrolysate, discoloration was significantly suppressed, in particular, even after storage for 2 days at 80° C. in the state of an aqueous solution (Experimental Example 2); therefore, this whey protein hydrolysate is useful as a whey protein hydrolysate in which deterioration in quality is inhibited during the production process and storage thereof.

Accordingly, the present invention provides a method for producing a whey protein hydrolysate that has the above desirable characteristics.

Figure 1:
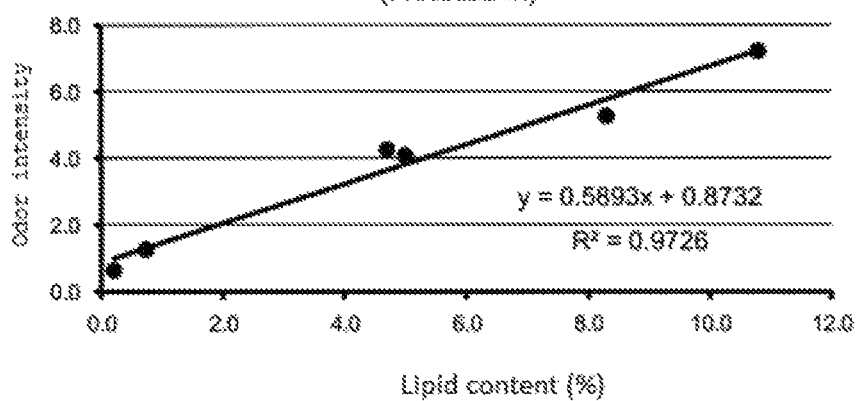
FIG. 1 is graphs showing the relationship between the lipid content of the whey protein-containing starting material and the odor intensity of the whey protein hydrolysis solution after enzymatic hydrolysis treatment. (A) shows the results obtained with the use of Protease M as an enzyme, and (B) shows the results obtained with the use of Protease P as an enzyme.
Figure 1:
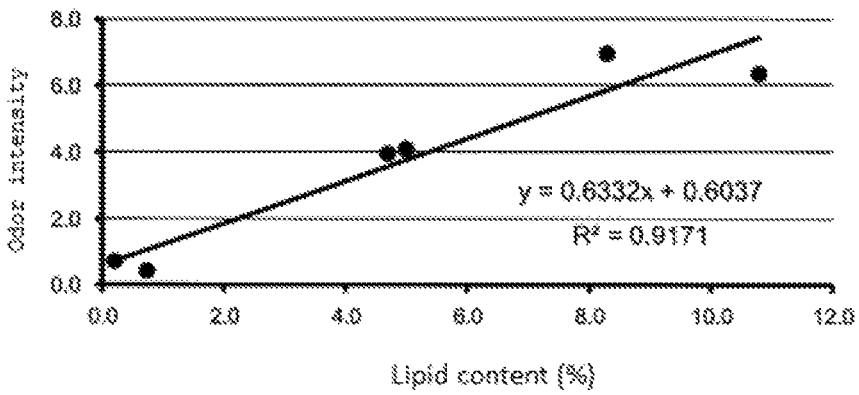

DESCRIPTION OF EMBODIMENTS (I) Method for Producing Whey Protein Hydrolysate (1) Production Starting Material The method for producing a whey protein hydrolysate of the present invention is characterized by using a whey protein-containing starting material having a lipid content of less than 1 mass % as a starting material for use in the production thereof.

Whey protein is a protein contained in whey (milk serum), which is a liquid portion obtained by removing casein and fat from milk; and is also called a milk serum protein. Whey usually contains β-lactoglobulin, α-lactalbumin, immunoglobulin, serum albumin, lactoferrin, and the like. The term "whey protein" as used in the present invention includes these individual proteins, as well as mixtures of two or more of these proteins.

Milk as the origin of whey is not limited, as long as it is mammal milk. Milk from cows (cow milk) is a preferable example, since it is widely applied to foods and beverages. About 80% of the protein contained in cow milk is casein, and the remaining roughly 20% is whey protein.

The whey protein-containing starting material used in the production of the whey protein hydrolysate of the present invention contains the whey protein described above, and has (a) a lipid content of less than 1 mass %, and/or (b) a lactose content of less than 1 mass %.

The whey protein-containing starting material satisfies at least one of the requirements (a) and (b) above. For the purpose of producing a whey protein hydrolysate having excellent flavor with less odor, the whey protein-containing starting material satisfies at least the requirement (a), and preferably satisfies both of the requirements (a) and (b). For the purpose of producing a whey protein hydrolysate in which time-dependent discoloration is suppressed, the whey protein-containing starting material satisfies at least the requirement (b), and preferably satisfies both of the requirements (b) and (a). The use of the whey protein-containing starting material that satisfies both of the requirements (a) and (b) enables the production of a whey protein hydrolysate having excellent flavor with less odor, and in which time-dependent discoloration is suppressed.

The term "odor" as used in the present invention refers to odor of a whey protein hydrolysate whose temperature is adjusted to room temperature, perceived by the nose. The expression "less odor" means that odor, in particular, odor characteristic to whey protein hydrolysates, is less intense than the odor of whey protein hydrolysates prepared by using a whey protein-containing starting material having a lipid content of more than 4 mass %, as shown in Experimental Example 1 described later. The term "flavor" as used in the present invention is a term collectively referring to the taste perceived when a whey protein hydrolysate whose temperature is adjusted to room temperature is held in the mouth, and the odor spread in the mouth and perceived through the nasal cavity. The expression "excellent flavor" means that the undesirable bitterness and rough taste, as well as unpleasant odor, characteristic to whey protein hydrolysates are reduced to a small degree, compared to those of whey protein hydrolysates prepared by using a whey protein-containing starting material having a lipid content of more than 4 mass %.

In the whey protein hydrolysate prepared by the above method using a whey protein-containing starting material having a lactose content of less than 1 mass % as a starting material, as shown in Experimental Example 2 described later, time-dependent discoloration is suppressed, compared to when a whey protein-containing starting material having a lactose content of more than 4 mass % is used. The suppression of time-dependent discoloration here can be evaluated according to the degree of the difference of absorbance (420 nm) before and after the storage of the whey protein hydrolysate for 2 days at 80° C. in a dark place, as shown in Experimental Example 2 described later.

The lipid content is less than 1 mass %, preferably 0.7 mass % or less, and more preferably 0.5 mass % or less. Further, the lactose content is also less than 1 mass %, preferably 0.7 mass % or less, and more preferably 0.5 mass % or less.

As long as the lipid content is less than 1 mass %, and/or the lactose content is less than 1 mass %, the whey protein-containing starting material may be whey itself (milk serum) that is prepared from milk; or, to an extent that whey protein does not undergo modification or quality changes, may be whey (milk serum) that has been processed with various treatment, such as extraction, filtration, fractionation, purification, condensation, or drying. As long as the lipid content is less than 1 mass %, and/or the lactose content is less than 1 mass %, commercially available whey or processed products thereof may also be used.

Protein Content

To efficiently obtain desired whey protein hydrolysates, the protein content of the whey protein-containing starting material is preferably 60 mass % or more, more preferably 80 mass % or more, and particularly preferably 90 mass % or more. Although the upper limit is 100 mass %, the content may be 98 mass %. In this specification, the protein content of the starting material can be measured following the Kjeldahl method.

The Kjeldahl method is a method for measuring the protein content of a measurement sample by determining the nitrogen amount in the sample. Specifically, a measurement sample mixed with sulfuric acid is heated to convert the nitrogen contained in the sample to ammonium sulfate. The resulting product is alkalized and heated, and the amount of the generated ammonia is quantified by appropriate titration. The following are more specific procedures. A measurement sample (about 0.5 g accurately weighed to 0.1 mg) is placed in a Kjeldahl flask, 10 g of decomposition accelerator (a powder mixture of 9 g of potassium sulfate and 1 g of copper(II) sulfate pentahydrate) is added thereto, and 15 mL of concentrated sulfuric acid is further added thereto, followed by mixing with shaking. Next, the resulting mixture is heated for 30 minutes in a block digester that has been kept warm at 200° C. beforehand. Thereafter, the temperature is set to 400 to 420° C., and after the decomposition solution becomes clear, decomposition is continued for about 60 minutes at 400 to 420° C. After the completion of decomposition, the temperature is cooled to room temperature, and 20 mL of ion-exchanged water is immediately added to the decomposition solution, followed by mixing with shaking. Thirty milliliters of ion-exchanged water and 25-45% (w/v) aqueous sodium hydroxide solution are added to the prepared decomposition solution, so that an excessive amount (24 g or more) of sodium hydroxide is present to alkalize the decomposition solution; thereafter, the flasks are connected to an ammonia distillation apparatus. At the outlet of the ammonia distillation apparatus, a 300-ml Erlenmeyer flask is provided that contains, as an ammonia trapping solution, an aqueous solution obtained by adding 2 to 3 drops of bromophenol blue solution as a titration indicator to 50 ml of 4% boric acid aqueous solution (prepared with ion-exchanged water), and distillation is performed to obtain 150 ml or more of distillate in the flask. The distillate obtained by distillation is titrated with a 0.05 mol/L sulfuric acid standard solution using a burette. The point at which the color of the distillate is changed from green to semitransparent to pale reddish-gray, is considered to be an end point; and the obtained titer ($V_1$: the volume of the sulfuric acid standard solution) is recorded to the second decimal point. Separately, as a blank experiment, sucrose in an amount equivalent to that of the measurement sample is collected in place of the measurement sample, and, as performed with the measurement sample, distillation is performed after decomposition; then, the titer ($V_2$: the volume of the sulfuric acid standard solution) is determined in a manner similar to the above. The nitrogen amount (g/100 g of whey protein-containing starting material) is calculated using the following formula to determine the nitrogen content (mass %) in 100 mass % of the whey protein-containing starting material.

Protein content (g/100 g)=nitrogen amount (g/100 g)× (nitrogen–protein conversion factor)

$$\text{Nitrogen amount}(g/100\ g) = \{[(V_1-V_2) \times f \times 1.4]/(W \times 1000)\} \times 100$$

$V_1$: the amount of 0.05 mol/L sulfuric acid standard solution used for neutralization in the experiment (mL).

$V_2$: the amount of 0.05 mol/L sulfuric acid standard solution used for neutralization in the blank experiment (mL).

f: the factor of 0.05 mol/L sulfuric acid standard solution used.

W: sampling amount (g).

The lipid content and the lactose content of the whey protein-containing starting material can be measured (quantified), for example, by the following methods.

Lipid Content Measurement Method

The lipid content of the whey protein-containing starting material can be measured following an acid hydrolysis method. The acid hydrolysis method is a method for obtaining lipid by extraction using a Mojonnier tube after decomposition of a measurement sample with hydrochloric acid. The following are more specific procedures. A mixture (10 ml) of water: 25-28% aqueous ammonia=9:1 is added to a measurement sample (W: the mass of about 1 to 1.5 g is accurately measured). Thereafter, concentrated hydrochloric acid (11 mL) is added thereto, and heat decomposition is performed on an electric heater (heating is performed to boiling, and maintained for 5 minutes after boiling). Subsequently, the sample after being cooled to room temperature is transferred to a Mojonnier tube, ethanol (10 mL) and diethyl ether (25 mL) are added thereto and mixed (the Mojonnier tube is washed with ethanol and diethyl ether), and petroleum ether (25 mL) is further added thereto for extraction. The Mojonnier tubes are centrifuged to separate an ether mixture layer from an aqueous layer, and the ether mixture layer is transferred to a separating funnel in which 30 mL of water is placed beforehand. Thereafter, a mixture of diethyl ether and petroleum ether (an equivalent mixture) is further added to the remaining ether mixture layer. After the same extraction operation as above is repeated twice, the ether mixture layer is transferred to the separating funnel (for the first extraction, 40 mL of diethyl ether/petroleum ether mixture is used; and for the second extraction, 30 mL of the mixture is used). The ether mixture collected in the separating funnel is sufficiently mixed by shaking with water, and left to stand. The separated water was discarded. The ether mixture was further washed twice with 30 mL of water. Sodium sulfate (anhydrous) is added to the collected ether mixture to absorb water, and the resulting product is collected by filtration in a fat bottle. The mass of the fat bottle ($W_0$) is measured beforehand after being dried in an electric constant-temperature dryer at 100 to 105° C. for one hour, and cooled. The solvent is distilled off from this ether mixture, and dried in an electric constant-temperature dryer at 100 to 105° C. for one hour, followed by cooling. The mass is then measured. Drying and cooling are repeated until the amount becomes constant, and the mass of the lipid ultimately obtained is accurately weighed in the fat bottle ($W_1$). Then, the amount of lipid (g/100 g) is calculated by the following formula, and the lipid content (mass %) in 100 mass % of the whey protein-containing starting material is calculated.

$$\text{Lipid content}(g/100\ g) = [(W_1 - W_0)/W] \times 100$$

$W_0$: the mass of the fat bottle (g)

$W_1$: the weight (g) of the fat bottle containing lipid after extraction and drying W: the sampling amount (g)

Lactose Content Measurement Method

The lactose content of the whey protein-containing starting material can be calculated by determining the protein content, lipid content, and ash content of the whey protein-containing starting material; and taking a content other than these contents as the lactose content. More specifically, the lactose content is obtained by deducting the protein content (mass %), lipid content (mass %), and ash content (mass %) of the whey protein-containing starting material from the mass (dry weight) of the whey protein-containing starting material, taking the mass (dry weight) of the whey protein-containing starting material as 100 mass %; i.e., [100-(protein content+lipid content+ash content)]. The protein content (mass %) and the lipid content (mass %) of the whey protein-containing starting material (100 mass %) can be obtained using the above methods.

The ash content can be measured following a direct ashing method. The following are more specific procedures. Roughly 0.4 to 1.2 g of a measurement sample is placed in a porcelain crucible whose weight is known ($W_0$), and the mass of the measurement sample ($W_1$) is accurately weighed. The resulting product is sufficiently incinerated at 550° C. in an incinerator (when the temperature reached 550° C., the temperature is maintained for 5 to 6 hours for incineration). After incineration, the measurement sample is cooled in a desiccator until the temperature thereof returns to room temperature, and the constant weight of the measurement sample ($W_2$) is accurately weighed. When the ash is white or gray, the sample is heated again for incineration at 550° C. for several hours, followed by cooling to determine the constant weight ($W_2$). The ratio of the mass of the measurement sample after incineration to the mass of the measurement sample before incineration is calculated using the following formula; and based on the obtained ash content (g/100 g), the ash content in 100 mass % of the whey protein-containing starting material (mass %) is determined.

$$\text{Ash content}(g/100\ g) = [(W_2 - W_0)/(W_1 - W_0)] \times 100$$

$W_0$: the mass (g) of the porcelain crucible as a constant weight $W_1$: the weight (g) of the porcelain crucible containing the sample before incineration $W_2$: the weight (g) of the porcelain crucible containing the sample after incineration (2) Production Method The method for hydrolyzing a whey protein-containing starting material is not particularly limited, as long as it is a method for hydrolyzing proteins. Examples include a method of treatment using a proteolytic enzyme (protease); a method of heat treatment in the presence of an acid or alkali; and the like. A method of treatment with a proteolytic enzyme is preferred.

The proteolytic enzyme used in the above enzymatic treatment is not limited, as long as it functions to hydrolyze the peptide bonds of a protein. Examples include animal-derived proteases, such as pepsin, chymotrypsin, trypsin, and pancreatin; plant-derived proteases, such as papain, bromelain, and ficin; endoproteases or exoproteases from microorganisms (e.g., *Lactobacillus*, *Bacillus subtilis*, filamentous fungi, actinomycetes, mold, and yeast); roughly purified products and fungal debris thereof; and the like. These may be used singly, or in an arbitrary combination of two or more. Those from microorganisms, in particular, endoproteases from filamentous fungi, are preferred.

Proteases are categorized into serine proteases (e.g., trypsin, and other alkaline proteases from *Bacillus subtilis*, the genus *Streptomyces*, and the genus *Aspergillus*), thiol proteases (e.g., papain), metal proteases (e.g., neutral proteases from *Bacillus subtilis*, the genus *Streptomyces*, and the genus *Aspergillus*), and aspartic proteases (e.g., pepsin, rennin, and other acidic proteases from the genus *Aspergillus*).

Preferred are proteases from the genus *Aspergillus*. Specific examples of such proteases that are commercially available include Protease M "Amano" SD and Protease P "Amano" 3SD (both are produced by Amano Enzyme, Inc.), "Kokulase P" (produced by Mitsubishi-Chemical Foods Corporation), "Flavourzyme" (produced by Novozymes), "Sumizyme FP" (produced by Shin Nippon Chemical Co. Ltd.), and the like.

The conditions for performing hydrolysis of whey protein with a protease, such as the pH, temperature conditions, and reaction time, can be appropriately selected and adjusted according to the types and combinations of proteases used; and the amount of the whey protein to be subjected to the hydrolysis treatment.

Although it is not limited, for example, in the method mentioned above for hydrolyzing whey with an acidic protease from the genus *Aspergillus*, the pH of whey is adjusted to pH 3.5 to 6.5, preferably pH 4.5 to 5.5; an acidic protease from the genus *Aspergillus* is added to the whey; and the mixture is slowly stirred to allow the reaction to proceed at 30 to 60° C., preferably 35 to 55° C., for 2 to 24 hours.

When the whey protein-containing starting material is treated by heating in the presence of an acid, the acid agent to be used may be, for example, but is not particularly limited to, hydrochloric acid, nitric acid, sulfuric acid, oxalic acid, and the like. The treatment conditions are not particularly limited, and can be arbitrarily selected according to the desired degree of hydrolysis. For example, the conditions may be appropriately selected from the ranges of the acid concentration of 0.1 to 3 mol/L, the heating temperature of 30 to 100° C., and the heating time of 1 to 50 hours.

When the whey protein-containing starting material is treated by heating in the presence of an alkali, the alkali agent to be used may be, for example, but is not particularly limited to, sodium hydroxide, potassium hydroxide, sodium carbonate, and the like. The treatment conditions are not particularly limited, and can be arbitrarily selected according to the desired degree of hydrolysis. For example, the conditions may be appropriately selected from the ranges of the alkali concentration of 0.1 to 3 mol/L, the heating temperature of 30 to 100° C., and the heating time of 1 to 50 hours.

(3) Product: Whey Protein Hydrolysate

The whey protein hydrolysate obtained by subjecting the whey protein-containing starting material to protease treatment, heat treatment in the presence of an acid, or heat treatment in the presence of an alkali usually has an average molecular weight (number average molecular weight) of, but is not particularly limited to, preferably about 5000 or less, and more preferably 200 to 1000. The average molecular weight can be measured by gel filtration chromatography. In this case, for example, pullulan and an aqueous solution are used as a standard polymer and an eluent, respectively, for producing "calibration curves."

The reaction product obtained by hydrolyzing the whey protein-containing starting material using the above methods may be directly used as a whey protein hydrolysate; or may be subjected to various treatments, such as fractionation, solid-liquid separation, filtration, condensation, drying, and sterilization, to use it as a whey protein hydrolysate. More specifically, the whey protein hydrolysates are a mixture of substances obtained by hydrolyzing the whey protein-containing starting material, the mixture containing whey peptides and amino acids, which are hydrolysates of whey protein itself.

The thus-prepared whey protein hydrolysate produced using a whey protein-containing starting material having a lipid content of less than 1 mass % as a starting material, as shown in Experimental Example 1 described later, has reduced odor characteristic to whey protein hydrolysates, reduced undesirable bitterness or rough taste characteristic to whey protein hydrolysates; and thus has excellent flavor, compared to the case where a whey protein-containing starting material having a lipid content of more than 4 mass % is used as a starting material. Moreover, as shown in Experimental Example 2 described later, when a whey protein hydrolysate is prepared by using the above method and using a whey protein-containing starting material having a lactose content of less than 1 mass % as a starting material, time-dependent discoloration is suppressed, compared to the case where a whey protein-containing starting material having a lactose content of more than 4 mass % is used.

The obtained whey protein hydrolysate may be used as an easily absorbable peptide material or a functional peptide material, by incorporating the whey protein hydrolysate into goods, such as foods (including beverages, the same applies hereinafter), medicinal drugs, quasi drugs, cosmetic products, or chemical products. In this specification, foods include general foods, health foods, sports foods, foods for elderly people, and oral or enteral nutrients. Health foods include dietary supplements, foods for specified health use, foods with health claims, foods with nutrient function claims, foods for promoting nutrition, and foods with function claims. These foods also include those in the form of a powder, a granule, a tablet, a jelly, a drink (ampoule), a hard capsule, and a soft capsule.

(II) Method for Reducing Odor, Enhancing Flavor, or Suppressing Discoloration of Whey Protein Hydrolysate The present invention also provides a method for reducing odor, enhancing flavor, or suppressing discoloration of whey protein hydrolysates.

The method for reducing odor of whey protein hydrolysates can be practiced by preparing a whey protein hydrolysate by hydrolyzing a whey protein-containing starting material having a lipid content of less than 1 mass %. The whey protein-containing starting material may further have a lactose content of less than 1 mass %. The whey protein-containing starting material, the hydrolysis treatment method, and the obtained whey protein hydrolysate are as described in (I) above, the disclosure of which is incorporated herein.

The method for enhancing the flavor of whey protein hydrolysates can be practiced by preparing a whey protein hydrolysate by hydrolyzing a whey protein-containing starting material having a lipid content of less than 1 mass %. The whey protein-containing starting material may further have a lactose content of less than 1 mass %. The whey protein-containing starting material, the hydrolysis treatment method, and the obtained whey protein hydrolysate are as described in (I) above, the disclosure of which is incorporated herein.

The method for suppressing time-dependent discoloration of whey protein hydrolysates can be practiced by preparing a whey protein hydrolysate by hydrolyzing a whey protein-containing starting material having a lactose content of less than 1 mass %. The whey protein-containing starting material may further have a lipid content of less than 1 mass %. The whey protein-containing starting material, the hydrolysis treatment method, and the obtained whey protein hydrolysate are as described in (I) above, the disclosure of which is incorporated herein.

Examples

The following Experimental Examples and Examples are provided to help further understanding of the structure and effects of the present invention. However, the present invention is not limited to these Experimental Examples and Examples. The procedures, treatments, or operations in the following Experimental Examples are performed under the conditions of room temperature and atmospheric pressure, unless otherwise specified. Room temperature refers to a temperature of 10 to 40° C.

Experimental Example 1

The relationship between the lipid content of the whey protein-containing starting material before protein hydrolysis, and the odor (unpleasant odor) or the flavor of the whey protein hydrolysate after hydrolysis was analyzed.

(1) Preparation of Samples

Six types of whey protein-containing starting materials having different lipid contents and different lactose contents (wheys A to F) were prepared, and subjected to tests. Table 1 shows the compositions (the protein content, lipid content, ash content, and lactose content) of the whey protein-containing starting materials (wheys A to F). The protein content, lipid content, and ash content of the whey protein-containing starting materials were determined following the Kjeldahl method, the acid hydrolysis method, and the direct ashing method, respectively, as described above. The lactose content was determined by calculation by deducting the amounts of protein, lipid, and ash from the whey protein-containing starting material, as described above.

TABLE 1

Composition of Whey Protein-Containing Starting Materials (100 mass %)

|  | Protein | Lipid | Ash | Lactose |
|---|---|---|---|---|
| Whey A | 98.0 | 0.2 | 1.8 | 0.0 |
| Whey B | 92.0 | 0.7 | 2.4 | 4.9 |
| Whey C | 86.4 | 5.3 | 3.8 | 4.5 |
| Whey D | 75.7 | 4.9 | 2.7 | 16.7 |
| Whey E | 66.1 | 8.7 | 3.4 | 21.8 |
| Whey F | 79.4 | 11.4 | 3.4 | 5.8 |

Each of the whey protein-containing starting materials (wheys A to F) (hereinbelow also referred to as "the substrates") (10 g) was dissolved in 190 g of water to obtain substrate liquids, to which Protease M (product name, Protease M "Amano" SD, produced by Amano Enzyme Inc., Japan) or Protease P (product name, Protease P "Amano" 3SD, produced by Amano Enzyme Inc., Japan) was added in an amount of 0.2 g (2 parts by mass based on 100 parts by mass (10 g) of the substrate weight); and the resulting mixture was reacted at 50° C. for 15 hours. Subsequently, the enzyme was deactivated by heat treatment at 80° C. for 60 minutes to obtain a total of 12 different types (2 types of enzymes×6 types of whey proteins) of whey protein hydrolysis solutions.

(2) Experiment Method

A sensory test was carried out by a panel of subjects consisting of 10 men and women in their 20s to 40s who had been well trained in the odor and taste of whey protein hydrolysis solutions, using 5-fold diluted solutions of the obtained whey protein hydrolysis solutions (hereinafter referred to as "the samples") to evaluate (A) the odor and (B) the flavor of the whey protein hydrolysis solutions.

Specifically, for the odor evaluation, the subjects (n=10) smelled through their nose the samples whose temperature was adjusted to room temperature, without holding the samples in the mouth; and evaluated the odor into 6 grades according to the following criteria (odor intensity).

Odor Determination Criteria
0: No odor was perceived at all.
2: Odor was perceivable (not unpleasant).
4: Slightly unpleasant odor was perceived.
6: Unpleasant, but not strong, odor was perceived.
8: Unpleasant odor was perceived.
10: Intense unpleasant odor was perceived.

For the flavor evaluation, the subjects (n=10) held in the mouth the samples whose temperature was adjusted to room temperature; and collectively evaluated the taste perceived when the sample was held in the mouth, and the odor spread in the mouth and perceived through the nasal cavity, into 7 grades according to the following criteria. More specifically, the sensory evaluation was performed based on the following criteria, in which the flavor of the 5-fold diluted solution of the hydrolyzed solution of whey A, which had the lowest lipid content, was taken as "standard 0." In the criteria, "+3: desirable flavor" indicates less bitterness, less rough taste, no unpleasant odor, and an easy-to-drink flavor.

Flavor Determination Criteria
+5: Very desirable flavor
+3: Desirable flavor
+1: Slightly desirable flavor
0: Equivalent to whey A
−1: Slightly undesirable flavor
−3: Undesirable flavor
−5: Very undesirable flavor (3) Experimental Results (A) Odor Evaluation According to the type of the enzymes (Protease M or Protease P) used in the hydrolysis treatment of the whey protein-containing starting material, FIG. 1 (A) (Protease M) and FIG. 1 (B) (Protease P) show the results in terms of the correlation between the average values of the results of the odor evaluated by each subject, and the lipid content of the whey protein-containing starting material used for the test.

These results revealed that the higher the lipid content of the whey protein-containing starting material before protein hydrolysis treatment, the more intense the odor (unpleasant odor) of the whey protein hydrolysate after hydrolysis treatment; and a positive correlation was observed between the lipid content of the whey protein-containing starting material and the odor (intensity) of the whey protein hydrolysate. That is, the results revealed that the use of the whey protein-containing starting material having a smaller lipid content in the preparation of a whey protein hydrolysate enables the production of a whey protein hydrolysate with less odor.

(B) Flavor Evaluation

Figure 2:
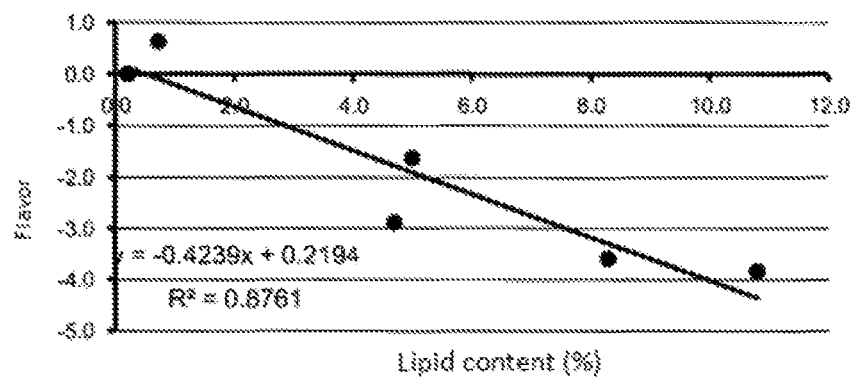
FIG. 2 is graphs showing the relationship between the lipid content of the whey protein-containing starting material and the flavor of the whey protein hydrolysis solution after enzymatic hydrolysis treatment. (A) shows the results obtained with the use of Protease M as an enzyme, and (B) shows the results obtained with the use of Protease P as an enzyme.
Figure 2:
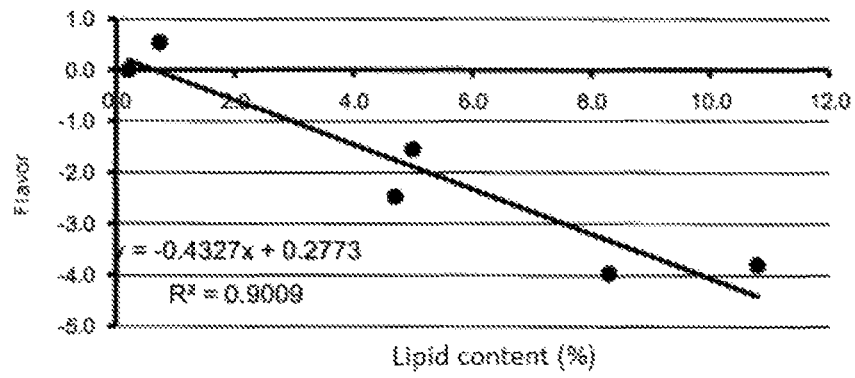

According to the type of the enzymes (Protease M or Protease P) used in the hydrolysis treatment of the whey protein-containing starting material, FIG. 2 (A) (Protease M) and FIG. 2 (B) (Protease P) show the results in terms of the correlation between the average values of the results of the flavor evaluated by each subject, and the lipid content of the whey protein-containing starting material used for the test.

These results revealed that the higher the lipid content of the whey protein-containing starting material before protein hydrolysis, the less desirable the flavor of the whey protein hydrolysate after hydrolysis; and a negative correlation was observed between the lipid content of the whey protein-containing starting material and the desirable flavor of the whey protein hydrolysate. That is, the results revealed that the use of the whey protein-containing starting material having a smaller lipid content in the preparation of a whey protein hydrolysate enables the production of a whey protein hydrolysate with desirable flavor.

Accordingly, to prepare a whey protein hydrolysate having a flavor (bitterness, rough taste, and unpleasant odor) that is excellent, with less odor, it is necessary to use a whey protein-containing starting material having a small lipid content, preferably a whey protein-containing starting material having a lipid content of 1 mass % or less, and more preferably less than 1 mass %, as a starting material (substrate).

Experimental Example 2

Figure 3:
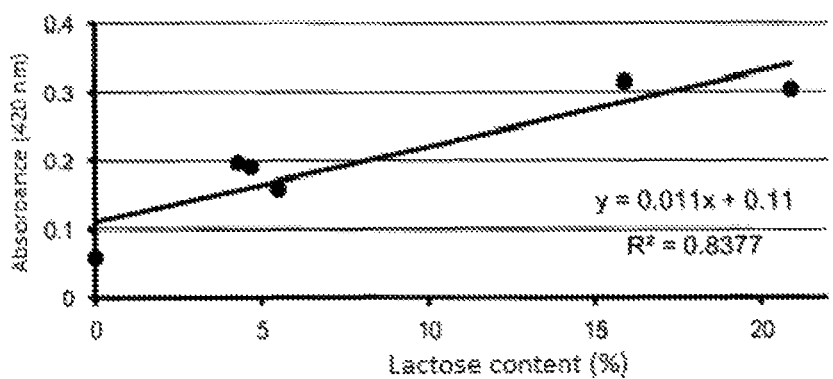
FIG. 3 is graphs showing the relationship between the lactose content of the whey protein-containing starting material and time-dependent discoloration of the whey protein hydrolysis solution after enzymatic hydrolysis treatment. (A) shows the results obtained with the use of Protease M as an enzyme, and (B) shows the results obtained with the use of Protease P as an enzyme.
Figure 3:
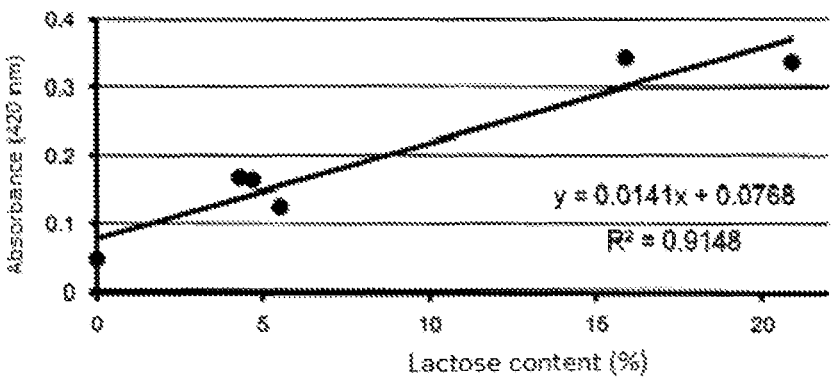

The relationship between the lactose content of the whey protein-containing starting material before protein hydrolysis, and the time-dependent discoloration of the whey protein hydrolysate after hydrolysis was analyzed.
(1) Experimental Method
The discoloration of the 12 different types of whey protein hydrolysis solutions prepared in Experimental Example 1 (2 types of enzymes (Protease M and Protease P)×6 types of whey proteins (wheys A to F)) was measured based on absorbance at 420 nm before and after the storage for 2 days at 80° C. in a dark place, and compared.
(2) Experimental Results
According to the type of the enzymes (Protease M or Protease P) used in the hydrolysis treatment of the whey protein-containing starting material, FIG. 3 (A) (Protease M) and FIG. 3 (B) (Protease P) show the results in terms of the correlation between the difference in the absorbance (420 nm) before and after the storage of the whey protein hydrolysis solution, and the lactose content of the whey protein-containing starting material used in the test.
These results revealed that the higher the lactose content of the whey protein-containing starting material before protein hydrolysis treatment, the greater the time-dependent discoloration of the whey protein hydrolysate after hydrolysis treatment; and a positive correlation was observed between the lactose content of the starting material and the discoloration of the whey protein hydrolysate. That is, the results revealed that the use of the whey protein-containing starting material having a smaller lactose content in the preparation of a whey protein hydrolysate enables the production of a whey protein hydrolysate that undergoes less time-dependent discoloration. Accordingly, to minimize time-dependent discoloration of the whey protein hydrolysate, it is necessary to use a whey protein-containing starting material having a small lactose content, in addition to a small lipid content, preferably a whey protein-containing starting material having a lactose content of 1 mass % or less, and more preferably less than 1 mass %, as a starting material (substrate).

The invention claimed is:
1. A method for producing a whey protein hydrolysate, the method comprising:
determining the mass percent of protein, lipid, ash, and lactose in a whey protein-containing starting material, wherein, when the lipid and lactose are present in the whey protein-containing starting material, the lipid content and the lactose content are each based on the total amount of protein, lipid, ash, and lactose in the whey protein-containing starting material taken as 100 percent mass, or wherein, when the lipid is present while the lactose is not present in the whey protein-containing starting material, the lipid content is based on the total amount of protein, lipid, and ash in the whey protein-containing starting material taken as 100 percent mass;
selecting the whey protein-containing starting material containing a lipid and either having (i) a lipid content of 0.2 mass percent or less, or having (ii) a lipid content of 0.2 mass percent or less and the lactose content of less than 1 mass percent; and
subjecting the selected whey protein-containing starting material to hydrolysis treatment.
2. The production method according to claim 1, wherein the lactose content of the selected whey protein-containing starting material is 0.5 mass percent or less.
3. The production method according to claim 2, wherein the method produces a whey protein hydrolysate that has bitterness which is reduced relative to bitterness of whey protein hydrolysates prepared using a whey protein-containing starting material having a lipid content of more than 4 mass percent, and
wherein the method produces a whey protein hydrolysate having an odor which is reduced relative to an odor of whey protein hydrolysates prepared using the whey protein-containing starting material having a lipid content of more than 4 mass percent.
4. The production method according to claim 2, wherein the method produces a whey protein hydrolysate in which time-dependent discoloration is suppressed more than in whey protein hydrolysates obtained by hydrolyzing a whey protein-containing starting material having a lactose content of more than 4 mass percent.
5. The production method according to claim 1, wherein the hydrolysis treatment is an enzymatic treatment.
6. The production method according to claim 5, wherein the enzymatic treatment is a treatment that uses a protease.
7. The production method according to claim 6, wherein the method produces a whey protein hydrolysate that has bitterness which is reduced relative to bitterness of whey protein hydrolysates prepared using a whey protein-containing starting material having a lipid content of more than 4 mass percent, and
wherein the method produces a whey protein hydrolysate having an odor which is reduced relative to an odor of whey protein hydrolysates prepared using the whey protein-containing starting material having a lipid content of more than 4 mass percent.
8. The production method according to claim 6,
wherein the whey protein-containing starting material has a lactose content of less than 1 mass percent, and
wherein the method produces a whey protein hydrolysate in which time-dependent discoloration is suppressed more than in whey protein hydrolysates obtained by hydrolyzing a whey protein-containing starting material having a lactose content of more than 4 mass percent.
9. The production method according to claim 6, wherein the protease is a protease from the genus *Aspergillus*.
10. The production method according to claim 6, wherein the protease is an acidic protease from the genus *Aspergillus*.
11. The production method according to claim 5, wherein the method produces a whey protein hydrolysate that has bitterness which is reduced relative to bitterness of whey protein hydrolysates prepared using a whey protein-containing starting material having a lipid content of more than 4 mass percent, and
wherein the method produces a whey protein hydrolysate having an odor which is reduced relative to an odor of whey protein hydrolysates prepared using the whey protein-containing starting material having a lipid content of more than 4 mass percent.

12. The production method according to claim 5,
wherein the whey protein-containing starting material has a lactose content of less than 1 mass percent, and
wherein the method produces a whey protein hydrolysate in which time-dependent discoloration is suppressed more than in whey protein hydrolysates obtained by hydrolyzing a whey protein-containing starting material having a lactose content of more than 4 mass percent.

13. The production method according to claim 1, wherein the method produces a whey protein hydrolysate that has bitterness which is reduced relative to bitterness of whey protein hydrolysates prepared using a whey protein-containing starting material having a lipid content of more than 4 mass percent, and
wherein the method produces a whey protein hydrolysate having an odor which is reduced relative to an odor of whey protein hydrolysates prepared using the whey protein-containing starting material having a lipid content of more than 4 mass percent.

14. The production method according to claim 1,
wherein the selected whey protein-containing starting material has a lactose content of less than 1 mass percent, and
wherein the method produces a whey protein hydrolysate in which time-dependent discoloration is suppressed more than in whey protein hydrolysates obtained by hydrolyzing a whey protein-containing starting material having a lactose content of more than 4 mass percent.

15. A method for producing a whey protein hydrolysate which has bitterness reduced relative to bitterness of whey protein hydrolysates prepared using a whey protein-containing starting material having a lipid content of more than 4 mass percent, and which has an odor reduced relative to an odor of whey protein hydrolysates prepared using the whey protein-containing starting material having a lipid content of more than 4 mass percent, the method comprising:
determining the mass percent of protein, lipid, ash, and lactose in a whey protein-containing starting material, wherein the lipid content is based on the total amount of protein, lipid, ash, and lactose in the whey protein-containing starting material taken as 100 percent mass;
selecting the whey protein-containing starting material containing a lipid and having a lipid content of 0.2 mass percent or less; and
subjecting the selected whey protein-containing starting material to hydrolysis treatment to prepare the whey protein hydrolysate.

16. The method according to claim 15, wherein the selected whey protein-containing starting material has a lactose content of less than 1 mass percent.

17. The method according to claim 15, wherein the hydrolysis treatment is an enzymatic treatment.

18. The method according to claim 17, wherein the enzymatic treatment is a treatment that uses a protease.

19. The method according to claim 18, wherein the protease is a protease from the genus *Aspergillus*.

20. The method according to claim 18, wherein the protease is an acidic protease from the genus *Aspergillus*.

21. A method for suppressing time-dependent discoloration of a whey protein hydrolysate more than in whey protein hydrolysates obtained by hydrolyzing a whey protein-containing starting material having a lactose content of more than 4 mass percent, the method comprising:
determining the mass percent of protein, lipid, ash, and lactose in a whey protein-containing starting material, wherein, when the lipid and lactose are present in the whey protein-containing starting material, the lipid content and the lactose content are each based on the total amount of protein, lipid, ash, and lactose in the whey protein-containing starting material taken as 100 percent mass, and wherein, when the lipid is present while the lactose is not present in the whey protein-containing starting material, the lipid content is based on the total amount of protein, lipid, and ash in the whey protein-containing starting material taken as 100 percent mass;
selecting the whey protein-containing starting material containing a lipid and having a lactose content of less than 1 mass percent and a lipid content of 0.2 mass percent or less; and
subjecting the selected whey protein-containing starting material to hydrolysis treatment to prepare the whey protein hydrolysate.

22. The discoloration suppressing method according to claim 21, wherein the lactose content of the selected whey protein-containing starting material is 0.5 mass percent or less.

23. The discoloration suppressing method according to claim 21, wherein the hydrolysis treatment is an enzymatic treatment.

24. The discoloration suppressing method according to claim 23, wherein the enzymatic treatment is a treatment that uses a protease.

25. The discoloration suppressing method according to claim 24, wherein the protease is a protease from the genus *Aspergillus*.

26. The discoloration suppressing method according to claim 24, wherein the protease is an acidic protease from the genus *Aspergillus*.

* * * * *